United States Patent [19]
Dorn

[11] Patent Number: 5,501,960
[45] Date of Patent: Mar. 26, 1996

[54] METHOD FOR IMPROVING QUANTITATIVE RECOVERY OF MICROORGANISMS FROM SPECIMENS CONTAINING BLOOD COMPONENTS

[76] Inventor: Gordon L. Dorn, 6647 Lakewood Blvd., Dallas, Tex. 75214

[21] Appl. No.: 396,262

[22] Filed: Feb. 27, 1995

Related U.S. Application Data

[63] Continuation of Ser. No. 162,664, Dec. 3, 1993, abandoned.

[51] Int. Cl.$^6$ ................................ C12Q 1/04; C12N 1/00
[52] U.S. Cl. ................................ 435/34; 435/4; 435/30; 435/243; 435/260; 435/803
[58] Field of Search ................................ 435/34, 4, 30, 435/243, 260, 803

[56] References Cited

U.S. PATENT DOCUMENTS

| | | | |
|---|---|---|---|
| 3,671,399 | 6/1972 | Cekoric, Jr. et al. | 195/100 |
| 3,875,012 | 4/1975 | Dorn et al. | 195/103.5 R |
| 3,883,425 | 5/1975 | Dorn | 435/34 |
| 3,928,139 | 12/1975 | Dorn | 195/103.5 R |
| 3,932,222 | 1/1976 | Dorn | 195/127 |
| 4,038,150 | 7/1977 | Dorn et al. | 195/127 |
| 4,131,512 | 12/1978 | Dorn | 195/103.5 M |
| 4,164,449 | 8/1979 | Dorn et al. | 435/30 |
| 4,212,948 | 7/1980 | Dorn | 435/4 |
| 4,666,850 | 5/1987 | Mehl et al. | 435/243 |
| 4,886,071 | 12/1989 | Mehl et al. | 435/34 |
| 5,070,014 | 12/1991 | Dorn | 435/34 |
| 5,081,033 | 1/1992 | Dorn et al. | 435/244 |
| 5,108,927 | 4/1992 | Dorn | 435/296 |

FOREIGN PATENT DOCUMENTS

| | | |
|---|---|---|
| 0572796 | 5/1988 | Australia . |
| 0143329 | 6/1985 | European Pat. Off. . |

OTHER PUBLICATIONS

Watanabe et al., *Chemical Abstracts*, vol. 83, p. 227, Ref. #39784x, 1975 (Riusho Boyi, 1975, 23(2) 148–152).

Escauialla et al, *J. Clin. Microbiol*, vol. 18, No. 2, pp. 380–383, Aug. 1983.

Dorn et al, *Chemical Abstracts*, vol. 110, p. 445 Ref. #169831x, 1989 (AU 572,796, May 19, 1988).

Reuiner et al, *J. Clin Microbiol*, vol. 21, No. 5, pp. 686–688, May 1985.

Murray et al, *J. Clin. Microbiol.* vol 29, No. 5, pp. 901–905, May 1991.

Technical Manual, Edited by R. H. Walker, 10th ed., American Association of Blood Banks, Arlington, VA, pp. 3–8, 19–24, 43–55, 634–641 (1990).

Merck Manual, Edited by R. Berkow, 16th ed., Merck & Co., Rahway, NJ, p. 1141 (1992).

Dorn et al., "New centrifugation blood culture device", *J. Clin Microbiol* 7:52–54 (1978).

Dorn, et al., "Blood culture technique based on centrifugation: developmental phase," *J. Clin Microbiol* 3:251–257 (1976).

Dorn et al., "Blood culture technique based on centrifugation: clinical evaluation," *J. Clin Microbiol* 3:258–263 (1976).

Braine, et al., "Bacterial sepsis secondary to platelet transfusion: an adverse effect of extended storage at room temperature," *Transfusion* 26:391–393 (1986).

Ulrich, et al., "Blood–borne infections associated with transfusion," *J. Intensive Care Med* 7:67–83 (1992).

Morrow, et al., "Septic reactions to platelet transfusions," *JAMA* 266:555–558 (1991).

Rawal, et al., "Dual reduction in the immunologic and infectious complications of transfusion by filtration/removal of leukocytes from donor blood soon after collection," *Transfusion Medicine Reviews* IV:36–41 (1990).

*Proceedings from the 36th Meeting of the Food and Drug Administration's Blood Products Advisory Committee.* Mimeographed transcript. Washington, D.C., May 1991.

Edberg et al., "Use of sodium polyanethol sulfonate to selectively inhibit aminoglycoside and polymixin antibiotic in a rapid blood level antibiotic assay," *Antimicrobial Agents and Chemotherapy* 9:414–417 (1976).

Belding, et al., "Effect of sodium polyanetholesulfonate on antimicrobial systems in blood", *Applied Microbiol* 24:691–698 (1972).

Sullivan, et al., "Practical aerobic membrane filtration blood culture technique: development of procedure", *J. Clin Microbiol* 1:30–36 (1975).

Tilton, R. C. "the laboratory approach to the detection of bacteremia," *Ann Rev Microbiol* 36:467–493 (1982).

Finegold, et al., "Evaluation of polyanethol sulfonate (Liquoid) in blood cultures", *Antimicrobial Agents and Chemotherapy*—:692–696 (1967).

Beebe, et al., "Effect of dilution on recovery of bacteria from blood," *J. Clin Microbiol* 5:448–452 (1977).

Salventi, et al., "Effect of blood dilution on recovery of organisms from clinical blood cultures in medium containing sodium polyanethol sulfonate," *J. Clin Microbiol* 9:248–252 (1979).

Evans, et al., "Comparative effects of anticoagulants on bacterial growth in experimental blood cultures," *American J Med Technol* 34:103–112 (1968).

Wilkins, et al., "Medium–dependent inhibition of *Peptostreptococcus anaerobius* by sodium polyanetholsulfonate in blood culture media," *J. Clin Microbiol* 3:393–396 (1976).

Eng. J., "Effect of sodium polyanethol sulfonae in blood cultures," *J. Clin Microbiol* 1:119–123 (1975).

(List continued on next page.)

Primary Examiner—Christina Y. Chan
Assistant Examiner—Abdel A. Mohamed
Attorney, Agent, or Firm—Richards, Medlock & Andrews

[57] ABSTRACT

A method for increasing the quantitation of microorganisms in cell-containing or cell-free blood samples, included those intended for blood product transfusion purposes, is provided which employs a sustained level of sodium polyanethol sulfonate throughout microbial replication on solid media. In another embodiment, purified saponin is combined with sodium polyanethol sulfonate to provide increased quantitation of microorganisms.

27 Claims, 6 Drawing Sheets

OTHER PUBLICATIONS

Rosner, R., "Comparison of recovery rates of various organisms from clinical hypertonic blood cultures by using various concentrations of sodium polyanethol sulfonate," *J. Clin Microbiol* 1:129–131 (1975).

Staneck, et al., "Inhibition of *Neisseria gonorrhoeae* by sodium polyanetholesulfonate," *J Clin Microbiol* 13:463–467 (1981).

Traub, et al., "Inactivation of classical and alternative pathway–activated bactericidal activity of human serum by sodium polyanetholsulfonate," *J Clin Microbiol* 5:278–284 (1977).

Kocka, et al., "Action of sulfated polyanions used in blood culture on lysozyme, complement and antibiotics," *Annals Clin Lab Sci* 2:470–473 (1972).

*Manual of Clinical Microbiology.* Edited by E. H. Lennette, 4th ed., American Society for Microbiology, Washington, D.C., pp. 75–76 (1985).

Finegold, S. M. and E. J. Baron, *Bailey and Scott's Diagnostic Microbiology*, 7th ed, C.V. Mosby Co., St. Louis, MO., pp. 210–224 (1986).

Guttierrez, et al., "Usefulness of a microblood culture technique in neonatal septicemia," *Archivos de Investigacion Medica* 11:129–136 (1980).

BLOCKING BACTERICIDAL ACTIVITY AGAINST *Y. enterocolitica* IN PLASMA

EFFECT OF SAPONIN, SPS, AND SAPONIN/SPS COMBINATION

Organism Count (cfu/ml) at Time Zero

- Untreated: 144
- Saponin: 12
- SPS (0.06%): 2832
- ISOLATOR 1.5: 2744
- Control Count: 2105

FIG. 3

BLOCKING BACTERICIDAL ACTIVITY AGAINST Y. enterocolitica IN PACKED RBCs

EFFECT OF SAPONIN, SPS, AND SAPONIN/SPS COMBINATION

Organism Count (cfu/ml) at Time Zero

- Untreated: 436
- Saponin: 1022
- SPS (0.06%): 812
- ISOLATOR 1.5: 3056
- Control Count: 3366

METHOD FOR IMPROVING QUANTITATIVE RECOVERY OF MICROORGANISMS FROM SPECIMENS CONTAINING BLOOD COMPONENTS

CROSS REFERENCE TO RELATED APPLICATIONS

This is a continuation of U.S. patent application Ser. No. 08/162,664 filed Dec. 3, 1993, now abandoned.

TECHNICAL FIELD

This invention relates to the field of analysis of microorganisms in a specimen containing blood or blood components.

BACKGROUND

Septicemia, which is the presence of pathogenic microorganisms in the blood, is one of the most serious types of infection encountered in modern medicine. Despite the armament of antimicrobial agents available today, the mortality rate for septicemia is approximately twenty-five percent, and when accompanied with septic shock, the mortality rate increases to about sixty percent. Patients suffering from debilitating diseases, undergoing major surgery, or receiving immunosuppressive drug therapy are especially prone to septicemia. Accurate, rapid quantitative analysis of blood specimens from patients suspected of septicemia is recognized as one of the most critical functions of clinical microbiology.

Transfusion of contaminated blood or blood products also represents a serious medical problem, often resulting in life-threatening septicemic shock or even death of the recipient. These risks are common for both autologous transfusions, where the blood donor is also the recipient, and homologous transfusions, where the blood donor is someone other than the recipient. Consequently, bacterial contamination of blood collected and processed by blood banks for transfusion represents a major threat to national blood supply and the national health.

The microorganisms associated with transfusion sepsis have certain characteristics. These organisms are capable of persisting in the blood for an extended period of time and often in high titers. It has been previously reported that introduction of a single organism into a platelet product can result in a final concentration of $10^4$ to $10^9$ colony forming units per milliliter (cfu/ml) of blood within three days at room temperature. (Braine, H., et al. 1986. Bacterial sepsis secondary to platelet transfusion: an adverse effect of extended storage at room temperature. *Transfusion* 26:391–393) They may exhibit a latent carrier state allowing an individual to be infected without manifesting any symptoms, or they may cause only subclinical infections. They are also stable in cold, stored blood. Among the microorganisms reported as being associated with transfusion sepsis are *Yersinia enterocolitica*, Pseudomonas sp., Achromobacter sp., *Escherichia coli*, Salmonella sp., *Staphylococcus epidermidis, Staphylococcus aureus*, Flavobacterium sp., and *Streptococcus viridans*. (Ulrich, P. and G. Vyas. 1992. Blood-borne infections associated with transfusion. *J. Intensive Care Med.* 7:67–83)

Identifying probable causes as well as possible solutions for transfusion sepsis requires knowledge of blood collection, process and storage. Whole blood obtained from "healthy" blood donors is routinely processed by blood banks to form various blood products which are subsequently transfused to patients for various purposes. A major source of possible donor blood contamination involves the collection of blood from an individual suffering from infection. During the infection process, microorganisms are seeded from the sight of infection into the bloodstream from which they are subsequently collected along with the donated blood. In an effort to prevent transfusion sepsis caused by transfusing blood collected from an individual suffering from infection, the donor's medical history is reviewed for situations which might signify an increased risk of harboring an infection, including exposure to infectious diseases by traveling to endemic areas; invasive procedures such as surgery, or social behavior such as homosexuality or drug addiction which are associated with increased risk of exposure to infectious diseases; or immunization against particular infectious agents. The donor is also given a physical examination which includes measuring the donor's body temperature as an indicator of possible infection. (*Technical Manual.* 1990. Edited by R. H. Walker, 10th ed., American Association of Blood Banks, Arlington, Va., pp. 3–8) Despite these attempts to screen infected donors, blood banks cannot adequately prevent blood collection from a donor who is dishonest when answering medical history questions or who unknowingly has a subclinical infection.

In a typical example of blood collection, approximately 450 milliliters of whole blood is collected from the donor by inserting a phlebotomy needle into a large vein in the donor's arm. The phlebotomy needle is connected to the delivery tubing leading into the primary blood collection bag. The needle insertion process also represents a major source of potential contamination. Despite procedures to disinfect the donor's arm with antimicrobial agents prior to phlebotomy, bacteria from the donor's skin, hair follicles, or sebaceous glands can enter a blood bag in the skin "core" cut out by the venipuncture needle. (Morrow, J., et al. 1991. Septic reactions to platelet transfusions. *JAMA* 266:555–558)

The primary bag contains an anticoagulant (e.g., citrate phosphate dextrose solution (CPD)) to prevent clotting, and during the collection process, the primary bag is inverted by a phlebotomist to disperse the anticoagulant evenly throughout the blood. Shortly after collection, the blood in the delivery tubing is "stripped" into the primary bag. After inverting the primary bag several times, the delivery tubing is allowed to refill with the anticoagulated blood. The delivery tubing is then heat-sealed into several detachable segments, providing samples of the collected blood for subsequent testing.

In blood processing, the whole blood donation is separated into various blood components. Historically, this process was performed in an "open" system where the blood was exposed to the environment during each separation procedure, and with exposure, the opportunity for contamination existed. In modern blood banking, blood processing is routinely performed using a closed blood bag system, where the primary bag has integrally attached satellite bags into which blood can be split into various blood products and subsequently stored without breaking hermetic seals, preventing exposure of the blood to the environment and possible contamination.

The primary bag of whole blood is first centrifuged at about 2100 rpm for about six minutes, causing the heavier red blood cells (RBCs) and about $1 \times 10^9$ white blood cells (WBCs) to sediment. The platelet-rich plasma, usually containing low numbers of RBCs and about $4 \times 10^7$ WBCs, is then expressed through connecting tubing from the primary bag into a satellite bag. The RBC sediment remaining in the primary bag contains approximately 210 milliliters (ml) RBCs, residual plasma, and anticoagulant. A red cell preservative solution (e.g., Adsol containing dextrose, sodium chloride, mannitol, and adenine) is added to the RBCs, producing approximately 300 ml packed red cells which currently have a shelf life of 42 days when stored at 6° C.

The satellite bag containing approximately 260 ml platelet-rich plasma and 60 ml anticoagulant may be centrifuged at about 3800 rpm for about three minutes, separating the platelets and from the plasma. The residual plasma and anticoagulant is expressed through connecting tubing into another satellite bag. The platelet concentrate containing approximately 45 ml platelet concentrate and 10 ml anticoagulant is then stored at 1°–6° C. for up to three days or on a rotator at 20°–24° C. for up to five days.

The plasma may be frozen within eight hours to produce fresh frozen plasma with a shelf life of one year when stored at −18° C. Alternately, it may be frozen, thawed, and then centrifuged at approximately 4200 rpm for five minutes to separate plasma (non-transfusable liquid recovered plasma) from cryoprecipitate which has a shelf life of one year when stored at −18° C. (*Technical Manual.* 1990. Edited by R. H. Walker, 10th ed., American Association of Blood Banks, Arlington, Va., pp. 43–55, 634–641)

Hemapheresis is another blood collection methodology which is becoming more prevalent in the blood banking industry. There are two categories of hemapheresis: 1) plasmapheresis for the collection of plasma and 2) cytapheresis for the collection of cellular blood components such as platelets and granulocytes. In these procedures, whole blood is removed from a donor; the blood is separated into components; the desired component is retained; and the remaining blood elements are recombined and returned to the donor. Cell separators utilize centrifugal force and the different densities of various blood components to achieve separation of the desired component. Platelet concentrates obtained by apheresis with a closed-system cell separator are stored at 1°–6° C. for up to three days or on a rotator at 20°–24° C. for up to five days; granulocyte concentrates, up to 24 hours at 20°–24° C. Many blood banks perform apheresis for the production of platelets and granulocytes preferentially over production from whole blood donations for a variety of reasons including: 1) the procedure can be performed more often than whole blood donation (once every forty-eight hours as opposed to once every fifty-six days) and 2) plateletpheresis typically yields a platelet unit volume equivalent to a pooled platelet unit made by combining seven to ten single platelet units obtained by processing whole blood donations. Clinicians in transfusion medicine report a reduction in serious antigen-antibody reactions due to the fact that the recipient is exposed to the antigenic properties of one person as opposed to the combined antigenic properties of multiple donors for a given transfusion. (*Technical Manual.* 1990. Edited by R. H. Walker, 10th ed., American Association of Blood Banks, Arlington, Va., pp. 19–24)

In apheresis procedures, the potential of contamination from infected donors and from the venipuncture needle "core" still exists. Most cytapheresis procedures utilize two venipunctures, inserting one phlebotomy needle into a vein of one arm for the removal of whole blood and another needle into a vein of the other arm for return of the remaining blood elements. This method of double phlebotomy increases the chances of contaminating the blood product.

Definitive steps have been taken in blood collection, processing and storage to reduce the possibility of bacterial contamination and subsequent transfusion sepsis. As mentioned previously, screening of blood donors in an attempt to prevent an individual suffering from an infection from donating blood, scrubbing regimens for cleaning the surface of the donor's arm, and the use of closed blood bag systems have decreased the risk of contaminated blood or blood products. Yet, despite these attempts to prevent or minimize contamination, transfusion sepsis continues to threaten the recipients of contaminated blood or blood products.

At a special session of the FDA's Blood Products Advisory Board on Yersinia contamination in platelets held in Washington, D.C. in May, 1991, several suggestions were presented as solutions to blood/blood product contamination: 1) attempting to improve the arm preparation prior to venipuncture, 2) adding antibiotics to the blood products, 3) shortening the storage time, 4) lowering storage temperatures, 5) holding blood at room temperature for several hours prior to processing and storage, 6) filtration, and 7) bacterial detection systems. It was concluded that surface disinfection of the arm does not eliminate contamination from the venipuncture needle "core" and improvements in arm preparation would not significantly lower the risk of transfusion sepsis. There was some skepticism concerning the effects of long term storage of antibiotics in the blood or blood product and its ultimate effect upon the transfusion recipient; therefore, the FDA Advisory Board did not consider applying this methodology to the problem of transfusion sepsis.

Another resolution suggested for the blood contamination crisis is to shorten the storage time allowed for blood and blood products. With the advent of closed blood bag systems and increased blood cell viability due to improvements in plastics chemistry, the storage time for certain blood products from the time of collection to the time of transfusion has been increased (RBC concentrates, from twenty-one to forty-two days; platelet products at room temperature, from three to seven days). Investigation of documented cases of transfusion sepsis have shown that the longer the storage time, the greater the risk of life-threatening transfusion sepsis. Severe medical complications resulting from the infusion of contaminated blood products has generally been associated with refrigerated units stored in excess of twenty-five days, and units stored at room temperature, five to seven days. Thus, it has been suggested that reducing the storage time for a blood product would lower its bioburden to "safe levels" for transfusion. However, shortening the allowable storage time for blood products does not totally eliminate the risk. Further, shortening storage times creates a serious imbalance between the public's blood requirements and available blood supply, producing a major negative impact on the cost effectiveness of blood centers and endangering the national blood supply.

Storing collected whole blood and most blood products at refrigeration temperature has also been suggested as a means of either preventing or reducing the growth of any bacteria introduced either from the donor blood or during the collection process. However, despite refrigeration of blood products, certain microorganisms routinely found in contaminated blood are capable of growing and reproducing from $10^2$ cfu/ml to concentrations of $10^8$ to $10^9$ cfu/ml when stored at refrigeration temperatures for 15 to 30 days.

The suggestion that whole blood be held at about 22° for 4 to 20 hours in order to exploit the natural self-sterilizing properties of blood as a method of improving the safety of the blood supply also fails to solve the problem. Blood has been reported to contain two basic types of immunity: (1) an innate, nonspecific immune mechanism consisting of phagocytes such as granulocytes and monocytes, and humoral components such as complement proteins, and (2) a learned, specific immune mechanism involving the antibody reactions of lymphocytes and immunoglobulins to antimicrobial antigens. At the time of collection, blood collected from a healthy, immunocompetent donor contains a significant number of phagocytes: approximately $3 \times 10^9$ WBCs, consisting of granulocytes (34%–83%), monocytes (3%–15%), and lymphocytes (12%–50%). (*Merck Manual.* 1992. 16th ed. (R. Berkow, ed.), Merck & Co, Rathway, N.J., p. 1141) While it is suggested that granulocytes will disintegrate within 1–5 days, monocytes are known to survive for over twenty days. Therefore, this approach to handling the blood supply relies on the donor being immunocompetent at the time of collection. Further, the immune response to the presence of microorganisms in the blood is first directed toward phagocytosis, which is facilitated by opsonization, or coating of a microorganism with antibody and/or complement proteins to promote its adherence and ingestion. Therefore, an effective immune response depends upon a successful antibody system, the activation of the complement cascade system and other humoral factors, and a intact phagocytic system. In practice, the attempt to exploit blood's self-sterilizing properties is ineffective because it is dependent on individual donor immunocompetence and it is thwarted by recommended storage conditions. Certain microorganisms such as *Yersinia enterocolitica* thrive at 4°–6° C., routine storage temperatures for stored blood. It is reported that humoral factors such as complement are inactivated and phagocytosis is reduced by about 70% at refrigeration temperatures. Moreover, it has been reported that phagocytized bacteria can only be killed by an oxidative burst which can occur only at higher temperatures such as 22°–37° C. (Pietersz, *Proceedings from the 36th Meeting of the FDA Blood Products Advisory Committee,* (1991)) Yet, to increase the viability of the RBCs, whole blood is routinely stored at 1°–10° C. prior to processing, if platelets are not to be prepared from the unit. After processing, many blood products are stored at 1°–6° C. Therefore, the self-sterilizing properties of the blood are blocked by recommended storage conditions.

The FDA Advisory Board concluded that research should be directed into the areas of leukocyte filtration and the development of bacterial detection systems for screening blood bank products for contamination. Leukocyte filtration devices have been developed for the production of leukopoor RBCs where WBCs, responsible for phagocytosis of microorganisms, are removed from the blood prior to processing in an effort to remove infectious agents and to reduce nonhemolytic transfusion reactions (e.g., graft versus host disease). (*Technical Manual.* 1990. Edited by R. H. Walker, 10th ed., American Association of Blood Banks, Arlington, Va.) (Ulrich, P. and G. Vyas. 1992. Blood-borne infections associated with transfusion. *J. Intensive Care Med.* 7:67–83)

In a study of various leukocyte filtration devices for the production of leukocyte-poor blood and blood products, the number of WBCs per packed RBC unit was reportedly reduced approximately 89% to 99%, or from about $4 \times 10^9$ WBCs/unit to about $10^7$–$10^9$ WBCs/unit. (Rawal, B., et al. 1990. Dual reduction in the immunologic and infectious complications of transfusion by filtration/removal of leukocytes from donor blood soon after collection. *Transfusion Medicine Reviews* IV:36–41) However, WBCs remaining in such filtered blood may contain microorganisms either phagocytized by or attached to the remaining WBCs. Subsequent rupturing of WBCs, either through natural death of the phagocyte over time or by mechanical disruption upon processing, will cause microorganisms to be released to contaminate the blood. Further, microorganisms can remain unassociated with WBCs, and filtration devices have not been shown to clear unattached bacteria from blood products. It is disclosed herein that certain bacteria may be associated with RBCs, and consequently, would not be removed from packed RBCs by a leukocyte filtering device.

Development of a rapid, sensitive, reliable, cost-effective test procedure which will identify contaminated blood products prior to transfusion has also been proposed. Suggested procedures for screening blood products include gram staining, acridine orange staining, endotoxin assay, and microbial cultural analysis. Gram staining requires a high concentration of bacteria of at least $10^5$–$10^6$ cfu/ml, and visualization of the bacteria is difficult due to the blood cells and bacteria staining the same color. Although acridine orange staining is more easily visualized with the blood cells staining pale green and the bacteria staining bright fluorescent orange, it is less sensitive, requiring greater than $10^5$–$10^6$ cfu/ml for detection. As a fluorescent staining technique, it is also susceptible to a high false positive/false negative rate. The endotoxin assay is a relatively expensive technique with a high false positive rate, requiring approximately $10^5$ cfu/ml. This procedure also fails to detect certain classes of bacteria which have been associated with transfusion sepsis (e.g., Staphylococcus species).

Another approach to identifying contaminated blood is conventional microbial cultural analysis. One method routinely used to detect septicemia in patients is the broth-based blood culture bottle system which is designed to encourage all microorganisms in a blood sample to replicate to a detectable level, thus providing qualitative-only microbial cultural analysis. A routine blood culture bottle contains a nutrient broth, e.g., tryptic soy broth, brain heart infusion, supplemented peptone, or thioglycolate broth, and an anticoagulant such as sodium polyanethol sulfonate (SPS) (Difco Laboratories, Detroit, Mich.) (BBL Microbiology Systems, Cockeysville, Md.). SPS is most commonly used in broth blood culture media at a concentration of 0.025%–0.03%. As an anticoagulant, SPS prevents clotting of the blood which would entrap the bacteria and prevent their detection. SPS is also reported to act as an anticomplementary and antiphagocytic agent, and to interfere with the antimicrobial action of aminoglycosides, providing further protection for the bacteria in the broth blood culture. In general, about 5 ml of blood is added to a blood culture bottle containing 45 ml of broth, representing a substantial dilution (1:10). This dilution, coupled with 0.03% SPS, generally provides adequate protection against complement and phagocytosis for the microorganisms to grow in the broth culture. The inoculated bottle is incubated at 35° C. and after twenty-four and forty-eight hours, a 0.1–0.5 ml aliquot of the blood culture is manually subcultured (i.e., blind subculture) onto routine nutritional agar medium (about 25 ml agar medium per 110×15 mm plate; hereinafter referred-to as "agar medium") such as blood agar or chocolate agar plates. The plates are incubated at 35° C. and are examined for microbial growth after twenty-four to forty-eight hours. The blood culture bottle is checked visually or growth/no growth detected via automated systems on a daily basis for up to seven to fourteen days for any evidence of microbial growth such as turbidity, hemolysis, gas production, or formation of discrete colonies. If visible growth is detected, the blood cultures are subcultured onto isolation media. At routine intervals, blind subcultures are performed. (*Manual of Clinical Microbiology,* 1985. Edited by E. H.

Lennette, 4th ed., American Association for Microbiology, Washington, D.C., pp. 75–76) (Finegold, S. M. and E. J. Baron. 1986. *Bailey and Scott's Diagnostic Microbiology,* 7th ed., C. V. Mosby Co., St. Louis, Mo., p. 217–218)

Basic broth blood culture methodology may require several days of incubation/subculture in order to obtain a pure isolate of a bacterium and yield minimal information (i.e., growth vs. no growth). If more than one organism is present in a patient blood sample, the more fastidious or slow growing organism is usually overgrown by fast-growing organisms and consequently is not detected. This methodology does not distinguish between "real" contamination in a blood sample versus laboratory contamination, i.e., contamination inadvertently introduced into the test system from the environment or by personnel during cultural analysis. Multiple broth blood cultures on one patient are usually performed, utilizing repetitive culturing of the same organism to distinguish between real and laboratory contamination. If broth-based methodologies are adopted for bacterial detection in blood bank products, any bacterial growth in the cultural analysis results in an automatic disposal of the blood product. Between 1% to 6% of all samples analyzed will yield inaccurate results due to laboratory contamination, representing a significant loss of blood product to the blood banking industry.

Another method of clinical microbial cultural analysis is the lysis-centrifugation procedure taught by Dorn et al. in U.S. Pat. No. 4,164,449 issued Aug. 14, 1979, and entitled "Surface Separation Technique for The Detection of Microbial Pathogens," and sold commercially as the ISOLATOR™10 (Carter-Wallace, Inc., Cranbury, N.J. 08512-0181) which contains 0.7 milliliters of an aqueous reagent containing 8 milliliters/liter polypropylene glycol (P-2000), 9.6 grams/liter sodium polyanethol sulfonate, 1 unit activity purified saponin, and 16 grams/liter ethylene diaminetetraacetic acid. In this procedure, patient blood is collected into a blood culture centrifugation tube which contains a chemical cocktail comprising a lysing agent of purified saponin (purified according to the procedure taught by Dorn in U.S. Pat. No. 3,883,425 issued May 13, 1975 and entitled "Detoxification of Saponins"; hereinafter referred to as "purified saponin" or "saponin", and hereby incorporated herein by reference), SPS as an anticoagulant, and ethylenediaminetetraacetic acid (EDTA) as a calcium chelator. In lysis-centrifugation methodology, about 10 ml of blood is collected into a blood culture centrifugation tube, and the tube is inverted several times to facilitate mixing of the sample with the cocktail and subsequent lysing of the blood. The lysed blood sample is then centrifuged, the supernatant discarded, and the sediment which contains the bacteria plated at about 0.3–0.5 ml per plate onto appropriate isolation solid agar media such as blood agar and chocolate agar. Within twenty-four to forty-eight hours, organisms cultured from the blood appear as discrete colonies on the isolation agar media. A lysis-only pediatric version covered by U.S. Pat. No. 4,164,449 described above and sold commercially as the ISOLATOR™1.5 (Carter-Wallace, Inc.) which contains 0.1 milliliters of an aqueous reagent containing 8 milliliters/liter polypropylene (P-2000), 9.6 grams/liter sodium polyanethol sulfonate, and 1 unit activity purified saponin, is also available to which 1.5 ml of blood is added to a formulation containing SPS and purified saponin as a lysing agent, and about 0.5 ml of the lysed blood is plated directly onto appropriate isolation solid agar media.

Certain aspects of the ISOLATOR™10 and ISOLATOR™1.5 methodologies are reported to be advantageous for clinical microbial analysis and would be applicable to blood banking. The presence of 0.06% SPS in the ISOLATOR™10 and ISOLATOR™1.5 is reported to inhibit the phagocytic activity of granulocytes and monocytes, and the normal antimicrobial activity of serum. (Finegold, S. M. and E. J. Baron. 1986. *Bailey and Scott's Diagnostic Microbiology,* 7th ed., C. V. Mosby Co., St. Louis, Mo., p. 221–222) Further, the lysis-centrifugation and lysis-only methodologies generally require twenty-four hours to not only obtain a pure isolate of a bacterium, but also to quantitate the number of bacteria per milliliter of blood. Using the quantitative aspect of the methodology, it would be possible to distinguish between real contamination in the blood product versus laboratory contamination (generally in the range of $\leq 10$ cfu/ml) if the bacterial count in the contaminated blood product is high, i.e., $\geq 10^2$ cfu/ml.

Although the problem of microbial contamination of blood has been recognized and various solutions attempted, there remains a need to identify potentially unsafe blood in a rapid and effective manner in order to provide for an effective balance between safety of the blood supply and having sufficient blood and blood products available to meet the needs of patients requiring transfusions.

A new method of quantitative microbial cultural analysis has now been found which results in a substantial improvement in microbial detection over the systems described above. By using this method to culture blood bank products held beyond "safe" periods (e.g., packed RBCs, $\geq 10$ days; platelets, $\geq 3$ days), it is possible to distinguish real blood product contamination from laboratory contamination. This methodology can also be utilized in improving quantitative blood cultures of septicemic patients. It is also applicable to the microbiological cultural analysis of veterinary specimens and of blood containing food products such as those encountered in the meat, poultry and seafood industries.

SUMMARY OF THE INVENTION

According to the invention, a method is provided to effectively block the bactericidal effects of the humoral components present in samples containing plasma during quantitative microbial analysis by sustaining the concentration of SPS at levels in excess of 0.01% beginning at the time of specimen collection and continuing throughout the plating of the specimen onto agar medium and the replication process. According to the invention, a modification of the above-described method is provided to effectively block the bactericidal effects of the cellular and humoral bactericidal components present in samples containing whole blood, packed RBCs, or platelets during quantitative microbial analysis by sustaining the concentration of SPS at levels in excess of 0.01% and the concentration of purified saponin beginning at the time of specimen collection and continuing throughout the plating of the specimen onto agar medium and the replication process. In a preferred embodiment of the present invention, SPS is incorporated into a treatment fluid for samples containing blood or blood products, whereupon plating said treated sample onto a microbiological agar medium, the final concentration of SPS is sufficient for effectively blocking the bactericidal components in the blood or blood product until said bactericidal components have been diluted to subcritical levels through diffusion into the microbiological agar medium. In a second preferred embodiment of the present invention, SPS is incorporated into a microbiological agar medium onto which a sample containing blood or blood product is plated, whereupon plating said sample onto said SPS containing microbiological agar medium, the final concentration of SPS is sufficient for blocking the bactericidal components in the blood or blood product until said bactericidal components have been diluted to subcritical levels through diffusion into the microbiological agar medium. An embodiment of this aspect comprises treating a sample with purified saponin as well as SPS in an effective concentration, beginning at the time of specimen collection and continuing throughout the plating of the specimen onto agar medium and the replication process. Another embodiment of this aspect comprises utilizing SPS containing microbiological agar medium which also contains purified saponin in an effective concentration.

According to the invention, any of the above embodiments can be used for microbial analysis of samples containing blood or blood components obtained from potentially septicemic patients, veterinary samples, blood or blood products in the blood banking industry, and blood containing food or dietary products.

In another aspect of the invention, methods for ascertaining the safety of blood products to be transfused into patients is provided which will allow blood banks to retain more of its blood products on a non-arbitrary basis.

DETAILED DESCRIPTION OF THE INVENTION

A novel method of microbial analysis is provided which utilizes effective amounts of sodium polyanethol sulfonate (SPS) alone or in combination with purified saponin, said effective amounts preferably being sustained over transport of a blood specimen to the laboratory and during replication of microbes-on solid media. It has been observed that methods previously taught in the art have not adequately addressed the cidal effects of blood on microorganisms, even though some methodologies have incorporated the use of SPS and/or purified saponin, because these components were not utilized in an optimum manner.

The natural antimicrobial properties of blood or blood products include powerful humoral bactericidal components as well as cellular phagocytic capabilities. Example 1 illustrates the powerful cidal potency of the humoral bactericidal components which may be found in blood containing specimens, where over 95% of the microorganisms inoculated into an undiluted plasma sample and immediately plated onto microbiological agar were killed. The results also suggest that while the effects of the plasma bactericidal components can be reduced by dilution, the cidal activity is not completely eliminated at a 1:10 dilution conventionally used in broth-based methods of microbial analysis.

With both the lysis-centrifugation and lysis-only quantitative techniques of microbial analysis, there is minimal dilution of the blood containing sample, and the SPS concentration at 0.06% is reported to block the bactericidal components in the blood from killing the microorganisms present. In Chart 1, the effective SPS concentrations are presented for each lysis treatment system, before and after plating. At 0.0012%, the SPS concentration is reduced well below the recommended protective range of 0.03% to 0.06%.

Chart 1: SPS Conc. in Various Lysis Treatment Methods

| Treatment | Final SPS conc in treatment | Plated volume | Final SPS conc in plated medium |
|---|---|---|---|
| Lysis-centrifugation | 0.06% | 0.5 ml[a] | 0.0012% |
| Lysis-only | 0.06% | 0.5 ml | 0.0012% |

[a]For the lysis-centrifugation method, about 0.3–0.5 ml in routinely subcultured. For comparative purposes, a 0.5 ml sample is shown.

It is herein disclosed for the first time that the protection provided by SPS incorporated into the lysis-centrifugation and lysis-only tubes is greatly reduced upon plating onto agar medium. When a sample is removed from one of these treatments and plated onto the surface of agar medium, the SPS, being of low molecular weight, rapidly diffuses into the agar, while the blood components diffuses at a much slower rate. With this reduction in SPS concentration upon plating, the bactericidal components in the blood or blood product, in turn, can become cidal again. Microbial death occurring after plating onto agar medium is hereinafter referred to as the "post-plating" bactericidal phenomenon. An example of post-plating death in a plasma sample is given in Example 2.

A solution to the above-described phenomenon is provided by sustaining the concentration of SPS and/or purified saponin at sufficient levels throughout each step of microbial analysis, from collection to subsequent growth in broth or on a microbiological agar plate, to greatly enhance the recovery of microorganisms from blood-containing samples by preventing post-plating death, hence increasing the sensitivity of the microbial analysis. In samples containing RBCs, e.g., packed red blood cells or whole blood, there is a synergic effect in combining sustained levels of SPS and purified saponin.

In this invention, purified saponin is utilized. Purified saponin is detoxified, that is, it is separated from substances found to be toxic to microorganisms by any method which will provide for separation of substances by M.W. cut-off of 10,000. A preferred method of purifying saponin is disclosed in U.S. Pat. No. 3,883,425, which is herein incorporated by reference. It should be recognized that this method can be modified using advances in filtering technology which accomplish the same separation result.

Sodium polyanethol sulfonate is the preferred component to be utilized in this invention. However, it should be recognized that other polyanionic sulfonates or analogues thereof may also work, and these are intended to be within the scope of this invention. For example, sodium polyamylosulfate (SAS) has been reported in the literature to have some similar activity to SPS.

The cell-free plasma experiment given in Example 2 demonstrates that the bactericidal components in the plasma can be blocked or reversed with appropriate levels of SPS. The protective effects of SPS are reversible; therefore, in a preferred embodiment of this invention, to maintain the blocking action of the humoral bactericidal components, minimal levels of SPS are sustained throughout the growth phase of the organism of interest.

In a method for microbial analysis of products or specimens containing blood cells (e.g., whole blood, packed RBCs, or platelets), purified saponin is also incorporated into the treatment system. When a blood or blood product containing RBCs, WBCs, or platelets is inoculated, it has been found that the microorganisms may be phagocytized or become attached to the outer surfaces of the blood cells. Upon plating and subsequent growth, the proximity of the microorganisms associated with a single blood cell results in the appearance of one colony for all microorganisms, rather than a distinct colony per microorganism. This problem has been addressed in this invention by the addition of purified saponin, an agent employed to release microorganisms from within or attached to cellular components of blood. The number of microorganisms recovered has been found to increase by employing saponin. A method for microbial analysis comprising sustaining the SPS and/or purified saponin concentrations throughout the culturing process for quantitative microbial analysis of blood containing specimens is provided. One treatment method for blood containing specimens comprises a tube containing purified saponin and SPS at concentrations which effectively sustain the purified saponin and SPS at sufficient concentrations to prevent death of the organisms throughout the culturing process. With this saponin/SPS tube treatment method, a sample of blood is added to the tube, and after 60 seconds to three hours, an aliquot is plated onto conventional agar medium for subsequent quantitation. A second treatment method comprises incorporating into conventional broth-based blood culture technology which contains SPS purified saponin to prevent death of the organisms upon plating onto either conventional agar medium or saponin/SPS-supplemented agar medium described below. For both methods, the final concentration of SPS upon plating is from about 0.005% to about 1%; preferably, from about 0.005% to about 0.1%; and most preferably, from about 0.005% to about 0.01%. The final concentration of purified saponin upon plating is from about 0.1 mg/ml to 20 mg/ml; preferably, from about 0.5 mg/ml to about 10 mg/ml; most preferably, from about 1.0 mg/ml to about 5.0 mg/ml. Both of these methodologies could be directly applied to culturing blood samples from patients suspected of septicemia.

A second embodiment comprises the incorporation of SPS or a saponin/SPS combination directly into conventional microbiological agar media. The final concentration of SPS incorporated into agar media is from about 0.005% to about 1%; preferably, from about 0.005% to about 0.1%; and most preferably, from about 0.005% to about 0.01%. The final concentration of purified saponin incorporated into agar medium is from about 0.1 mg/ml to 20 mg/ml; preferably, from about 0.5 mg/ml to about 10 mg/ml; most preferably, from about 1.0 mg/ml to about 5.0 mg/ml. The incorporation of saponin and/or SPS directly into an agar plated medium can be used to prevent post-plating death caused by the presence of humoral bactericidal components present in clinical samples contaminated with blood or blood components which are cultured directly onto plates, i.e., throat or wound swabs, tissue samples, or spinal or pleural fluids.

The saponin/SPS-supplemented agar medium of the invention is applicable to the culturing of blood bank products. By first allowing growth amplification of the low numbers of organisms in blood products through delayed testing, direct plating of blood products onto the saponin/SPS-supplemented agar medium provides a means to discriminate between true contamination from laboratory contamination and thereby ascertain the sterility of packed RBCs held beyond ten to forty-two days and platelets held beyond one to seven days.

Moreover, both the saponin/SPS tube or plate methodology could find further utility in the quantitative microbial analysis of veterinary samples or meat products. The potential value in this case is based upon the assumption that bactericidal components found in animal blood are similar to those found in human blood.

EXAMPLE 1

EFFECT OF DILUTION ON THE BACTERICIDAL COMPONENT IN PLASMA

A culture of *Yersinia enterocolitica* ATCC (American Type Culture Collection, Rockville, Md.) #23715 on chocolate agar was incubated at 36° C. overnight. About two to three colonies of the organism were transferred via sterile swab from the chocolate agar culture into a 5 ml Mueller-Hinton broth culture tube, which was then incubated on a rotator for about two to three hours at 36° C. Using a spectrophotometer set at a wavelength of 630 nm, the turbidity of broth culture was adjusted by the addition of Mueller-Hinton broth to an optical density equivalent to $1 \times 10^8$ cfu/ml. A series of five 1:10 dilutions of the broth culture were prepared in sterile phosphate buffered saline (PBS), producing an inoculum solution.

A plasma unit was inoculated with about 0.5 ml of the PBS inoculum solution, yielding a final concentration of approximately $1 \times 10^3$ cfu/ml, given as the saline control count in Table 1. The inoculated plasma units were held at room temperature throughout the experiment.

At Time Zero, samples of the inoculated plasma were transferred from the unit into empty sterile test tubes. Using sterile phosphate buffered saline (PBS), the plasma samples were diluted to create a dilution series of 100%, 50%, 25%, and 10% (v/v) plasma. A 0.5 ml aliquot from each plasma dilution was plated onto each of two chocolate agar plates. At 15 minute intervals for up to 60 minutes, the plasma dilution tubes were vortexed for about ten seconds and 0.5 ml of the tube contents were plated onto each of two chocolate agar plates. The inoculated chocolate agar plates were held at 36° C. for 24–48 h, and the colonies on each plate were counted.

Figure 1:
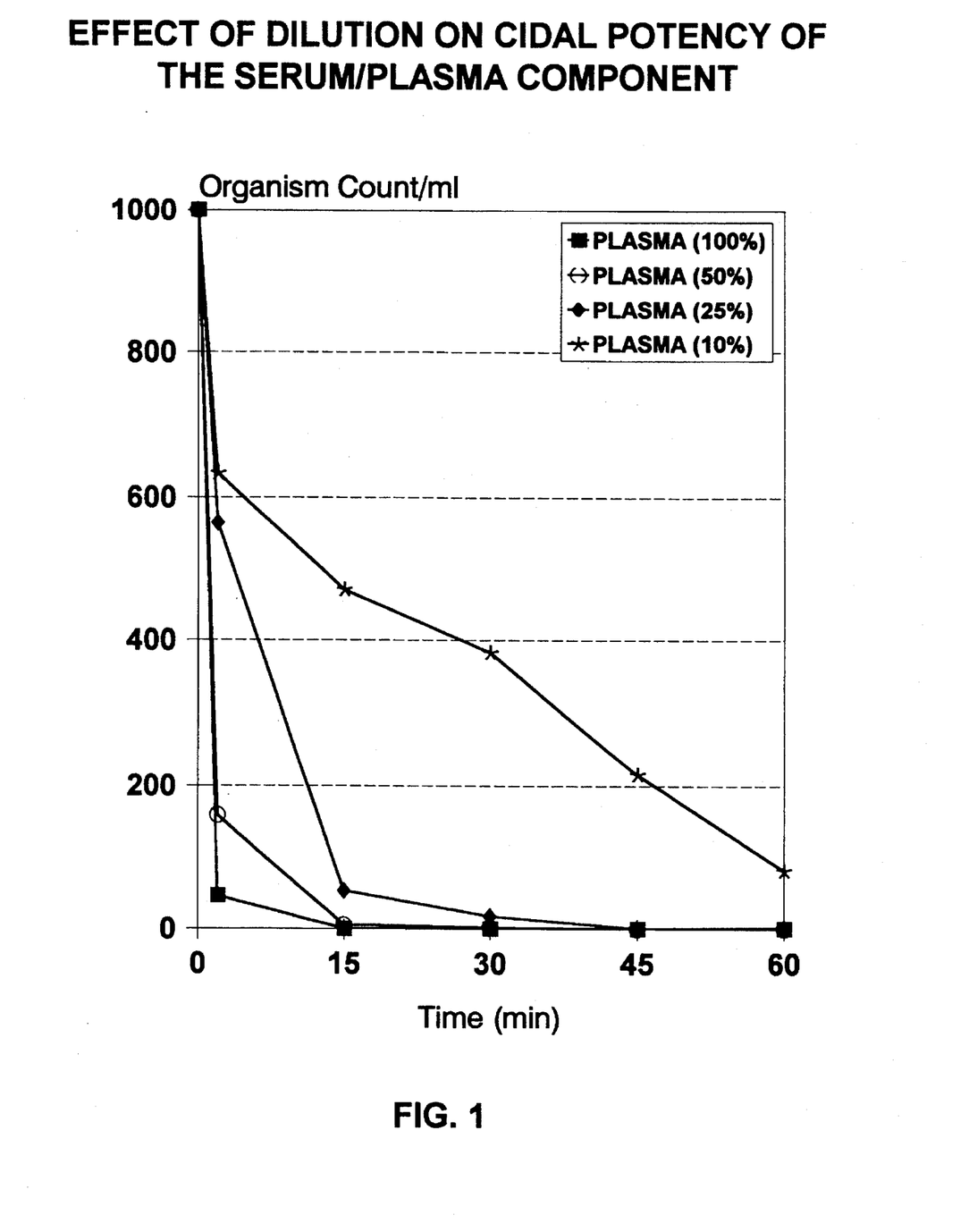
FIG. 1 is a graph depicting the antimicrobial activity of a bactericidal component in plasma and the effects of dilution upon the bactericidal activity.

Table 1 and FIG. 1 demonstrate the potency of the bactericidal components in plasma. Plating undiluted plasma (100%) at Time Zero resulted in a loss of over 95% of the organisms. A 3-log loss in organism count was obtained within 15 minutes exposure to undiluted plasma. Even at 10% (v/v), or a 1:10 dilution, 90% of the organisms were killed in one hour.

TABLE 1

EFFECT OF DILUTION ON BACTERICIDAL COMPONENT IN PLASMA

| Plasma Concentration | Organism Count (cfu/ml) Over Time[a] Incubation Time (min) | | | | |
|---|---|---|---|---|---|
| | 0 | 15 | 30 | 45 | 60 |
| 100% | 46 | 0 | 0 | 0 | 0 |
| 50% | 159 | 6 | 2 | 0 | 0 |
| 25% | 564 | 54 | 18 | 1 | 2 |
| 10% | 633 | 471 | 383 | 216 | 83 |

[a]Saline control count = 1000 cfu/ml.

EXAMPLE 2

BLOCKING BACTERICIDAL ACTIVITY AGAINST *Y. enterocolitica* IN PLASMA BY SUSTAINING SPS CONCENTRATION The "SPS" tubes were prepared by aseptically adding about 0.1 ml of 9%, 4.5%, and 1.5% (w/v) sterile aqueous SPS solutions into empty sterile test tubes, where upon addition of 1.5 ml plasma, the final concentration of SPS was 0.6%, 0.3%, and 0.1%, respectively. For tubes containing 0.06% SPS, the commercially available ISOLATOR™ 1.5 tubes (Carter-Wallace, Cranbury, N.J.) were used. Upon addition of 1.5 ml of plasma, the final SPS concentration in the ISOLATOR™1.5 was about 0.06%. Sterile, empty test tubes were utilized with untreated samples.

A transfusable unit of human plasma was obtained from a local blood bank. An inoculum solution of *Yersinia enterocolitica* ATCC #23715 was prepared according to the procedure given in Example 1. The unit was inoculated with about 0.5 ml of the PBS inoculum solution, yielding a final concentration of approximately $1 \times 10^3$ cfu/ml, expressed as the saline control count in Table 2. The inoculated plasma unit was held at room temperature throughout the experiment. At Time Zero and at 15 minute intervals for up to 90 minutes, the plasma units were inverted several times to produce a homogeneous suspension. Using a multiple-entry port, samples were removed from each inoculated plasma unit and processed in duplicate by adding 1.5 ml of plasma into one of the following treatment tubes, vortexing the contents of the tube for about ten seconds and then plating 0.5 ml of the tube contents onto each of two chocolate agar plates: 1) a sterile empty tube (Untreated); 2) 0.1% SPS tube; 3) 0.3% SPS tube; 4) 0.6% SPS tube, and 5) ISOLATOR™1.5 tube. The inoculated chocolate agar plates were held at 36° C. for 24-48 h, and the colonies on each plate were counted.

Figure 2:
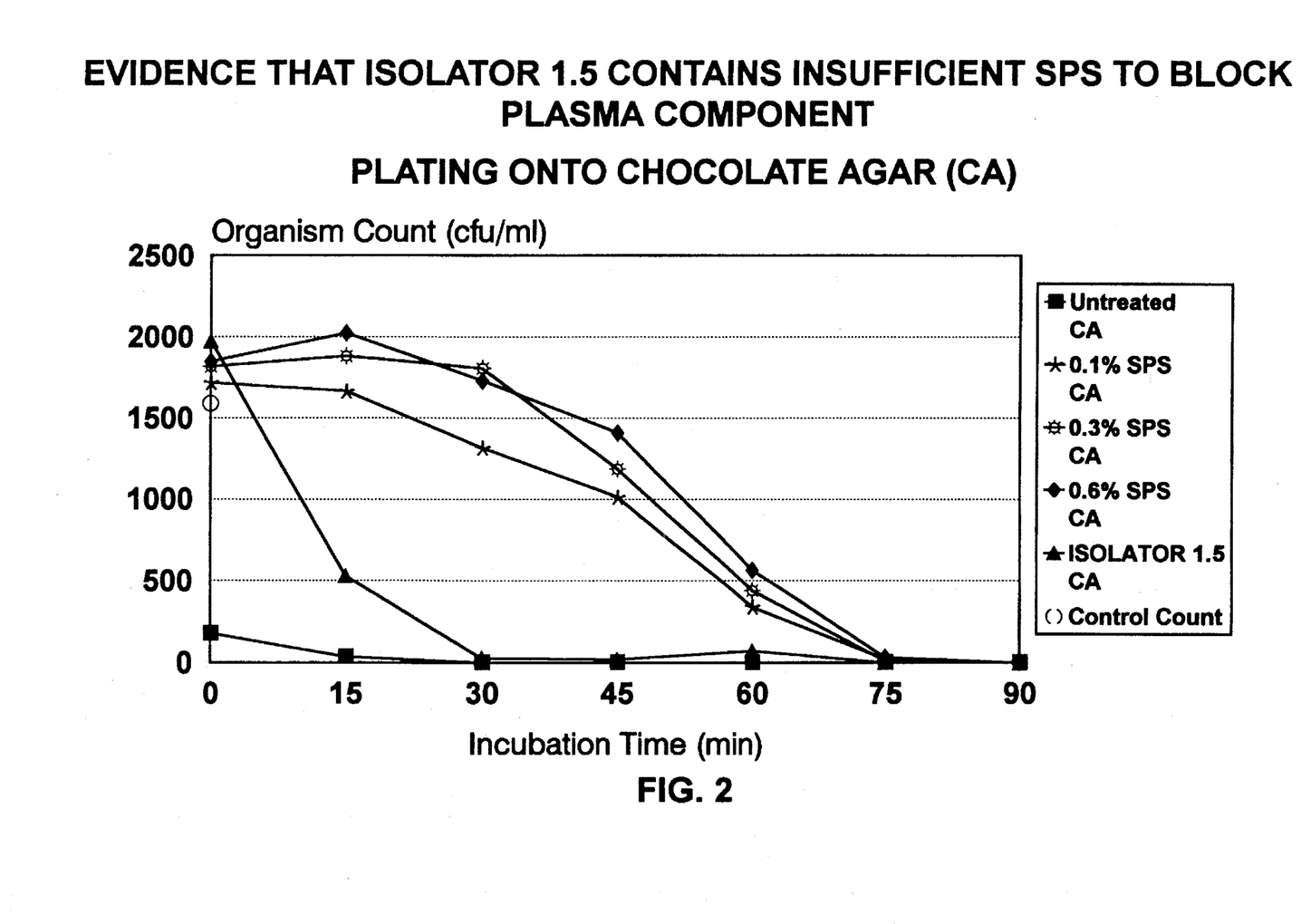
FIG. 2 is a graph depicting the antimicrobial activity of bactericidal components in plasma and the blocking action of SPS at various concentrations.

As shown in Table 2 and FIG. 2, post-plating death occurs when Untreated plasma is plated on a conventional agar medium at Time Zero: only 180 cfu/ml were recovered from 1589 cfu/ml, representing a loss of about 90% of the organism count. This difference in organism count between the saline control count and the Untreated sample at Time Zero represents the degree of post-plating death. Moreover, the number of microorganisms actually present in the plasma sample at the Time Zero plating is evident in the organism count for samples protected by the SPS (e.g., 1846 cfu/ml for 0.6% SPS), which is essentially equivalent to the saline control count.

Treatment with the ISOLATOR™1.5 (0.06% SPS) prevented post-plating death at Time Zero, but this low concentration of SPS was insufficient in preventing substantial loss in organism count at subsequent time points. After a thirty minute exposure to the bactericidal components prior to treatment with 0.06% SPS and plating, only 28 cfu/ml were recovered, representing a loss in organism count.

By comparison, increasing the SPS treatment concentrations to 0.1%, 0.3%, and 0.6% resulted in complete recovery at Time Zero and recovery of 59%, 63%, and 76% of the original counts, respectively, after thirty minutes exposure to the bactericidal components in plasma prior to SPS treatment and plating. Thus, sustaining the SPS concentration at greater than or equal to 0.1%, or greater than or equal to 0.6% prior to plating, provided greatly enhanced recovery in plasma.

TABLE 2

BACTERICIDAL ACTIVITY AGAINST *Y. enterocolitica* IN PLASMA Blocking by Sustaining SPS Concentration

| Treatment Tube | Organism Count Over Time (cfu/ml)[a] Incubation Time (min) | | | | | | |
|---|---|---|---|---|---|---|---|
| | 0 | 15 | 30 | 45 | 60 | 75 | 90 |
| Untreated | 180 | 36 | 0 | 0 | 0 | 0 | 0 |
| 0.1% SPS | 1716 | 1664 | 1315 | 1012 | 340 | 22 | 0 |
| 0.3% SPS | 1816 | 1880 | 1804 | 1186 | 438 | 10 | 0 |
| 0.6 SPS | 1846 | 2022 | 1728 | 1408 | 564 | 32 | 0 |
| ISOLATOR ™ 1.5 (0.06% SPS) | 1974 | 528 | 28 | 19 | 72 | 0 | 0 |

[a]Saline control count = 1589 cfu/ml.

EXAMPLE 3

BLOCKING BACTERICIDAL ACTIVITY AGAINST *Y. enterocolitica* IN MATCHING PACKED RBCs AND PLASMA BY SPS, PURIFIED SAPONIN, AND SAPONIN/SPS COMBINATION The Saponin tubes were prepared by aseptically adding about 0.1 ml of a sterile 1.5% (w/v) aqueous purified saponin solution into empty sterile test tubes, and upon addition of 1.5 ml of blood product, the purified saponin concentration was about 0.1%. The 0.06% SPS tubes were prepared by aseptically adding about 0.1 ml of a sterile 0.9% (w/v) aqueous SPS solution into empty sterile test tubes, and upon addition of 1.5 ml of blood product, the final SPS concentration was about 0.6%. For tubes containing both purified saponin and 0.06% SPS, the commercially available ISO-LATOR™1.5 (Carter-Wallace, Cranbury, N.J.) were used, and upon addition of 1.5 ml of blood product, the final SPS and purified saponin concentrations were about 0.06% and 0.1%, respectively. Sterile, empty test tubes were utilized with untreated samples.

A transfusable unit of packed RBCs and plasma produced from the same blood donation (matched) were obtained from a local blood bank. An inoculum solution of *Yersinia enterocolitica* ATCC #23715 was prepared according to the procedure given in Example 1. Each unit was inoculated with about 0.5 ml of the PBS inoculum solution, yielding a final concentration of approximately $1 \times 10^3$ cfu/ml, expressed as the control counts in Table 3. The inoculated packed RBC and plasma units were held at room temperature throughout the experiment.

At Time Zero, each unit was inverted several times to produce a homogeneous suspension. Using a multiple-entry port, samples were removed from each unit and processed in duplicate by adding 1.5 ml of the blood product into one of the following treatment tubes, vortexing the contents of the tube for about ten seconds and then plating 0.5 ml of the tube contents onto each of two chocolate agar plates: 1) a sterile empty tube (Untreated); 2) Saponin tube; 3) 0.06% SPS tube; and 4) ISOLATOR™1.5 tube. The inoculated chocolate agar plates were held at 36° C. for 24–48 h, and the colonies on each plate were counted.

Figure 3:
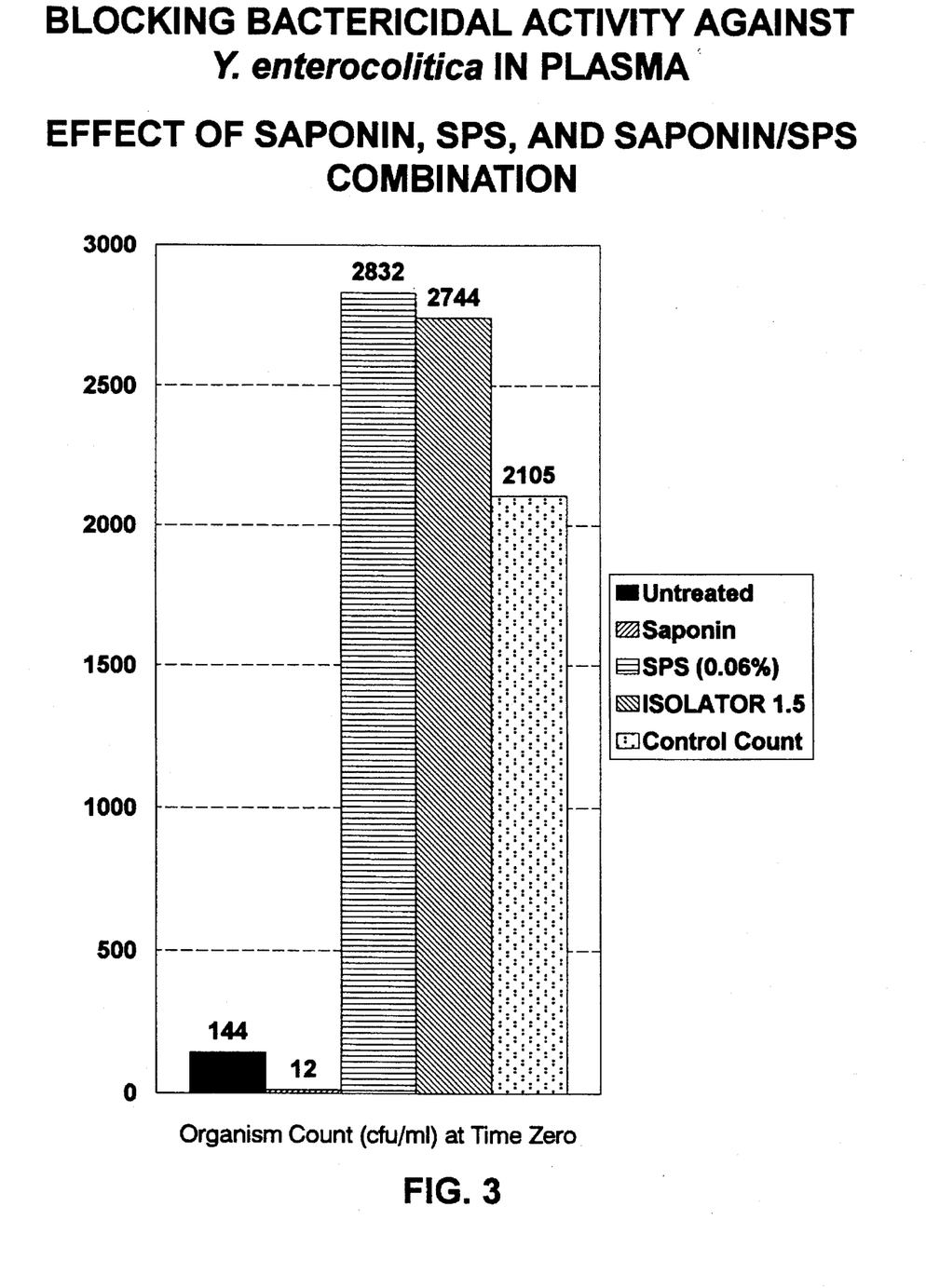
FIG. 3 is a graph depicting the antimicrobial activity of bactericidal components in plasma and the blocking action of SPS, purified saponin, and a saponin/SPS combination.
Figure 4:
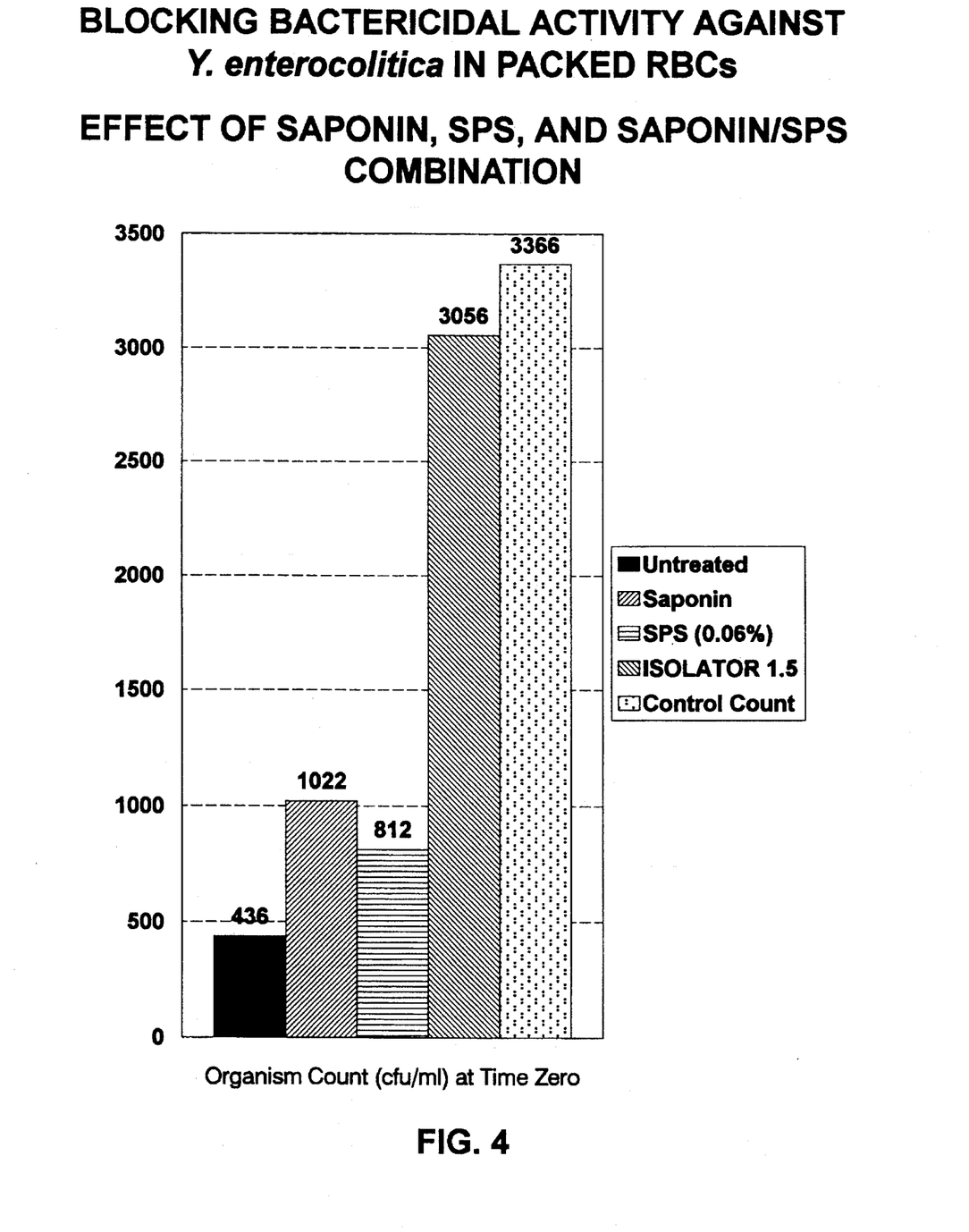
FIG. 4 is a graph depicting the antimicrobial activity of bactericidal components in packed RBCs and the blocking action of SPS, purified saponin, and a saponin/SPS combination.

The results are given in Table 3, and graphically represented in FIG. 3 and FIG. 4. The results demonstrate the effect of purified saponin, SPS, and the combination of saponin and SPS upon the bactericidal components found in specimens containing plasma and in specimens containing plasma and blood cells. In plasma, 93% of the organisms were killed in the Untreated sample at Time Zero, representing potent bactericidal activity. Treatment of the inoculated plasma before plating with 0.06% SPS and the ISOLATOR™1.5 (saponin/SPS combination) completely blocked the bactericidal components in the plasma, while treatment with purified saponin did not prevent death. This suggests that the purified saponin has no beneficial action on the recovery of microorganisms from cell-free plasma containing samples.

In matching packed RBCs, only 436 cfu/ml out of 3366 cfu/ml were recovered from the Untreated sample plated at Time Zero, representing a loss of 87% in organism count. Treatment of the inoculated packed RBCs with 0.06% SPS resulted in a recovery of 30%. The recovery rate for treatment with purified saponin was slightly less at 24%. However, when the inoculated packed RBCs was treated with a combination of 0.06% SPS and purified saponin (ISOLATOR™1.5), 91% of the organisms were recovered, representing a synergic effect between the SPS and saponin.

TABLE 3

BACTERICIDAL ACTIVITY AGAINST *Y. enterocolitica*
IN MATCHED PACKED RBCs AND PLASMA
Blocking by SPS, Saponin, and Saponin/SPS Combination

| Treatment tube | Organism Count (cfu/ml) at Time Zero | |
| --- | --- | --- |
| | Plasma | Packed RBCs |
| Untreated | 144 | 436 |
| Saponin tube | 12 | 1022 |
| 0.06% SPS tube | 2832 | 812 |
| ISOLATOR ™ 1.5 (Saponin + 0.06% SPS) | 2744 | 3056 |
| Control count | 2105 | 3366 |

EXAMPLE 4

BLOCKING BACTERICIDAL ACTIVITY AGAINST *Y. enterocolitica* IN PACKED RBCs PRELYSIS OF RBCs BY PURIFIED SAPONIN PRIOR TO TREATMENT WITH SPS Modified chocolate agar plates supplemented with SPS were prepared as follows. About 0.1 ml of a sterile 15% (w/v) aqueous SPS solution was aseptically spread across the surface of a commercially prepared chocolate agar plate (BBL Microbiology Systems, Detroit, Mich.) (CA plates). The plates were incubated at room temperature overnight to allow the SPS to diffuse throughout the agar. The final SPS concentration in the modified chocolate agar plates was about 0.06%.

A transfusable unit of packed RBCs was obtained from a local blood bank. Using transfer packs, the unit was split into two units of equal volume. One "prelysed" unit was prepared by aseptically adding a sufficient amount of purified saponin solution to provide a final concentration of about 0.1% (w/v). An inoculum solution of *Yersinia enterocolitica* ATCC #23715 was prepared according the the procedure given in Example 1. Each transfer pack was inoculated with about 0.5 ml of the PBS inoculum solution, yielding a final concentration of approximately $1 \times 10^3$ cfu/ml, expressed as the saline control count in Table 4. The inoculated packed RBC units were held at room temperature throughout the experiment.

At Time Zero and at 15 minute intervals for up to 90 minutes, the inoculated packed RBC transfer packs were inverted several times to produce a homogeneous suspension. Using a multiple-entry port, samples were removed from each inoculated transfer pack and processed in duplicate by plating 0.5 ml either onto conventional chocolate agar (CA) or onto SPS-supplemented chocolate agar plates (SPS/CA). The inoculated agar plates were held at 36° C. for 24–48 h, and the colonies on each plate were counted.

Figure 5:
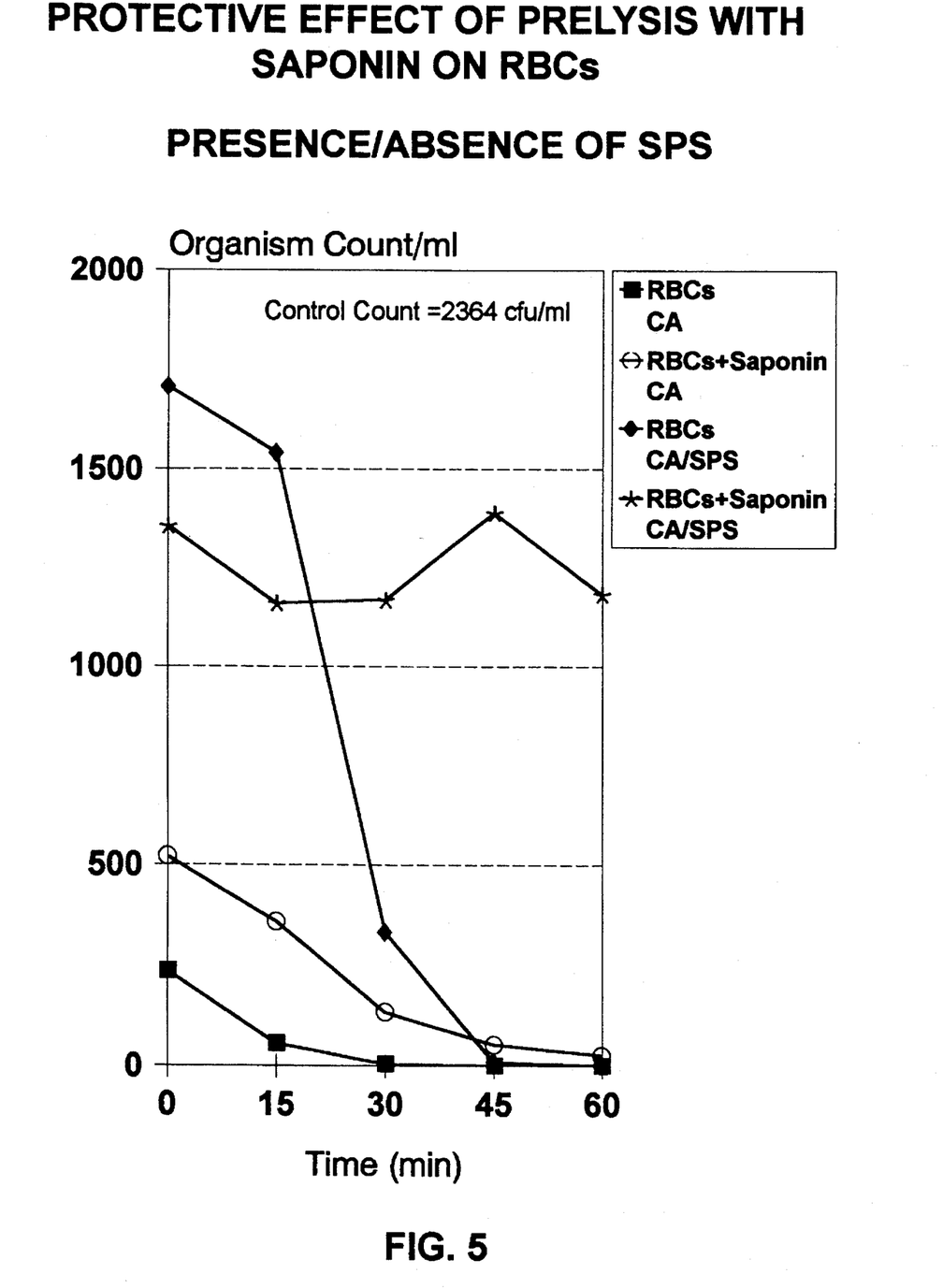
FIG. 5 is a graph depicting the antimicrobial activity of bactericidal components in packed RBCs and the effects of prelysis with purified saponin prior to treatment with SPS.

The results of this experiment are given in Table 4 and graphically depicted in FIG. 5. Plating onto chocolate agar at Time Zero, the Untreated sample showed a 90% loss in organism count. It is believed that by prelysing the packed RBCs with purified saponin prior to inoculation, cellular bactericidal components such as phagocytosis and/or attachment of the microorganisms to the blood cells are essentially blocked, and an increase in recovery rates due to the detachment of microorganisms would not be anticipated. This is evident in the minimal increase (2.2-fold) in organism count when plated on chocolate agar at Time Zero. Also, as indicated in cell-free plasma, it would not be anticipated that purified saponin would offer protection from the cidal activity of the humoral bactericidal components in the blood containing specimen. However, at each time point, greater recovery was noted for the prelysed vs. the unlysed sample, and the difference between the two systems increases over time: about 2.2–, 6.4–, 33.3–, 53–, and $\geq$108-fold. Therefore, it is disclosed herein that through the lysing action of purified saponin, resultant lysed cellular components of blood are released which offer some protection from humoral bactericidal activity.

Plating the unlysed and prelysed inoculated packed RBCs onto SPS-supplemented chocolate agar plates demonstrated that the incorporation of SPS into the agar medium functions similarly to an SPS treatment tube in that post-plating death was blocked by the SPS. Further, plating onto the SPS-supplemented agar plates did not prevent death which occurred in the blood prior to the SPS treatment, hence the decrease in organism counts over time. However, when blood cells were prelysed prior to inoculation and plating onto SPS-supplemented agar, the purified saponin/SPS combination prevented not only post-plating death, but also death prior to exposure to SPS and organism count was maintained over time.

TABLE 4

BACTERICIDAL ACTIVITY AGAINST *Y. enterocolitica*
IN PACKED RBCS
Prelysis with Purified Saponin Prior to Treatment with SPS

| Pre-inoculation Treatment | Plating Medium | Organism Count Over Time (cfu/ml) Incubation Time (min) | | | | |
|---|---|---|---|---|---|---|
| | | 0 | 15 | 30 | 45 | 60 |
| Untreated | CA | 235 | 56 | 4 | 1 | 0 |
| Saponin | CA | 520 | 359 | 133 | 53 | 27 |
| Untreated | SPS/CA | 1707 | 1540 | 333 | 10 | 1 |
| Saponin | SPS/CA | 1354 | 1160 | 1168 | 1388 | 1182 |

<sup>a</sup>Saline control count = 2364 cfu/ml

EXAMPLE 5

BLOCKING BACTERICIDAL ACTIVITY AGAINST *Y. enterocolitica* IN PACKED RBCs INCORPORATION OF SPS, PURIFIED SAPONIN, AND SAPONIN/SPS COMBINATION INTO AGAR MEDIUM Modified chocolate agar plates were prepared by aseptically spreading about 0.2 ml of the following sterile aqueous solutions across the surface of a commercially prepared chocolate agar plate (BBL Microbiology Systems, Detroit, Mich.) (CA plates): 1) 25% (w/v) purified saponin, producing a 0.2% saponin plate (Saponin/CA); 2) 7.5% (w/v) SPS, producing a 0.06% SPS plate (SPS/CA); and 3) a solution containing and 25% (w/v) purified saponin and 15% (w/v) SPS, producing a 0.2% Saponin plus 0.06% SPS plate (Saponin/SPS/CA). The plates were incubated at room temperature overnight to allow the saponin and/or SPS to diffuse throughout the agar. The Saponin tubes were prepared by aseptically adding about 0.1 ml of a sterile 3.0% (w/v) aqueous purified saponin solution into empty sterile test tubes, and upon addition of 1.5 ml of blood product, the purified saponin concentration was about 0.2%.

A transfusable unit of packed RBCs was obtained from a local blood bank. An inoculum solution of *Yersinia enterocolitica* ATCC #23715 was prepared according the the procedure given in Example 1. The packed RBCs unit was inoculated with about 0.5 ml of the PBS inoculum solution, yielding a final concentration of approximately 1×10³ cfu/ml, expressed as the saline control count in Table 5. The inoculated packed RBC units were held at room temperature throughout the experiment.

At Time Zero, the inoculated packed RBC transfer packs were inverted several times to produce a homogeneous suspension. Using a multiple-entry port, samples were removed and processed in duplicate by 1) plating 0.5 ml onto a conventional chocolate agar plate (CA); 2) plating 0.5 ml onto one of each of the supplemented chocolate agar plates (Saponin/CA; SPS/CA; Saponin/SPS/CA); and 3) adding 1.5 ml to a Saponin tube followed by plating 0.5 ml onto a conventional chocolate agar plate. The inoculated agar plates were held at 36° C. for 24–48 h, and the colonies on each plate were counted.

Figure 6:
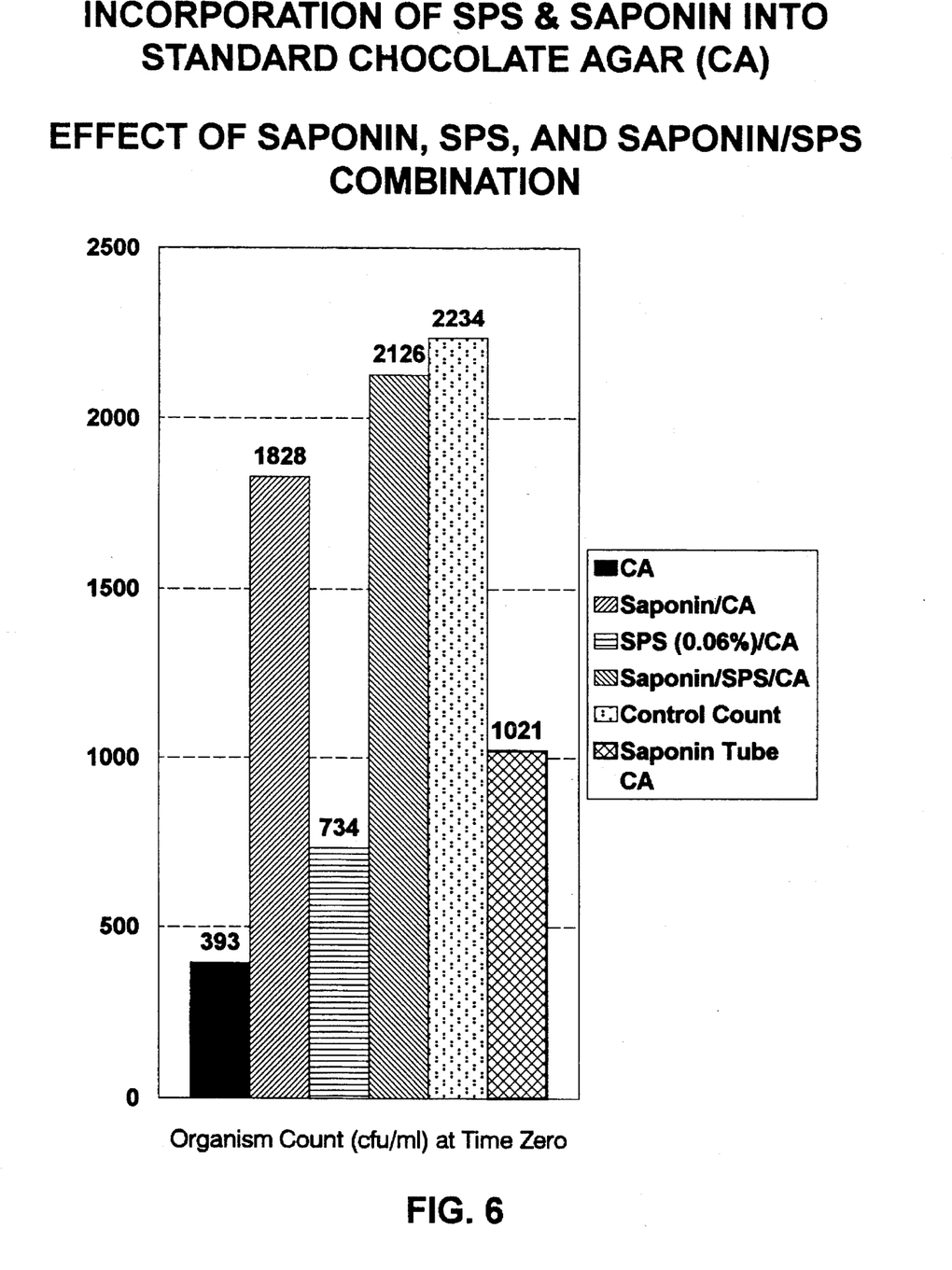
FIG. 6 is a graph depicting the antimicrobial activity of bactericidal components in packed RBCs and the blocking action of SPS, purified saponin, and a saponin/SPS combination incorporated into agar medium.

The results of this experiment are given in Table 5 and graphically depicted in FIG. 6. The potency of the bactericidal components in packed RBCs is demonstrated in the loss of over 82% of the organisms when a Untreated sample is plated onto chocolate agar. The recovery rate for the Saponin/SPS/CA plate was essentially 100%, indicating that purified saponin and SPS can be incorporated into an agar plate as opposed to the Saponin/SPS treatment tube given in Example 3. With the purified saponin incorporated into an agar plate, the importance of sustaining purified saponin is more pronounced when compared to the Saponin tube, as evidenced by the 82% recovery rate for the Saponin/CA plate vs. the 46% recovery rate with the Saponin tube. Moreover, the synergic relationship between purified saponin and SPS was not demonstrated with the Saponin/SPS/CA plate.

TABLE 5

BACTERICIDAL ACTIVITY AGAINST *Y. enterocolitica*
IN PACKED RBCS
Incorporation of SPS, Purified Saponin,
and Saponin/SPS Combination into Agar Medium

| Treatment | Plating Medium | Organism Count (cfu/ml) at Time Zero |
|---|---|---|
| None | CA | 393 |
| None | Saponin/CA | 1828 |
| None | SPS/CA | 734 |
| None | Saponin/SPS/CA | 2126 |
| Saponin tube | CA | 1021 |

<sup>a</sup>Saline control count = 2234 cfu/ml

EXAMPLE 6

BLOCKING BACTERICIDAL ACTIVITY AGAINST *Y. enterocolitica* IN WHOLE BLOOD SAPONIN/0.6% SPS TUBE vs. UNTREATED The saponin/0.6% SPS tubes were prepared by aseptically adding about 0.05 ml of a sterile 1.8% (w/v) aqueous SPS solution and about 0.05 ml of a sterile 3.0% (w/v) aqueous purified saponin solution into empty sterile test tubes, and upon addition of 1.5 ml of whole blood, the final SPS concentration was about 0.6% and the purified saponin concentration about 0.1%.

Transfusable unit of whole blood were obtained from a local blood bank. An inoculum solution was prepared for a wide range of gram negative and gram positive microorganism according to the procedure given in Example 1. Each whole blood unit was inoculated with about 0.5 ml of the PBS inoculum solution, yielding a final concentration of approximately 1×10³ cfu/ml. The whole blood units were held at room temperature throughout the experiment.

After two hours incubation, the inoculated whole blood units were inverted several times to produce a homogeneous suspension. Using a multiple-entry port, samples were removed and processed in duplicate by 1) plating 0.5 ml onto a conventional chocolate agar plate (CA) and 2) adding 1.5 ml to a saponin/0.6% SPS tube followed by plating 0.5 ml onto a conventional chocolate agar plate. The inoculated agar plates were held at 36° C. for 24–48 h, and the colonies on each plate were counted.

Table 6 and Table 7 present the results of these experiments in terms of increased recovery provided by the saponin/0.6% SPS-treated sample over the recovery obtained from the untreated sample for gram negative and gram positive organisms, respectively. The overall average improvement for gram positive and gram negative organisms was 280-fold, ranging from 0.3-fold for *Streptococcus pneumoniae*, an organism known to be sensitive to SPS, to 10,030-fold for *Escherichia coli*. Highly significant increases in the rate of recovery many gram negative microorganisms were observed. The wide ranges of recovery suggests the improvements are donor-dependent and organism-dependent.

TABLE 6

BACTERICIDAL ACTIVITY AGAINST
GRAM NEGATIVE ORGANISMS IN WHOLE BLOOD
Saponin/0.6% SPS Tube vs. Untreated

| Organism | No.[a] | Increased Recovery (#-fold improvement) | |
|---|---|---|---|
| | | Avg. | Range |
| *Escherichia coli* (3)[b] | 9 | 1675 | 2–10030 |
| *Hemophilus influenzae* | 1 | 1483 | — |
| *Yersinia enterocolitica* (3) | 14 | 1450 | 8–6610 |
| *Alcaligenes faecalis* | 4 | 1093 | 385–2717 |
| *Salmonella choleraesuis* | 3 | 1049 | 725–1310 |
| *Citrobacter freundii* | 3 | 751 | 98–1287 |
| *Salmonella typhi* | 3 | 338 | 621 |
| *Citrobacter diversus* | 3 | 271 | 22–743 |
| *Klebsiella pneumoniae* (2) | 8 | 226 | 1–906 |
| *Pseudomonas putida* | 2 | 209 | 131–287 |
| *Pseudomonas fluorescens* | 2 | 185 | — |
| *Enterobacter agglomerans* (2) | 9 | 117 | 2–559 |
| *Pseudomonas aeruginosa* (2) | 8 | 117 | 2–572 |
| *Neisseria meningitidis* (2) | 11 | 105 | 1–498 |
| *Enterobacter aerogenes* | 3 | 56 | 13–107 |
| *Serratia marcescens* | 1 | 23 | — |
| *Morganella morganii* | 3 | 22 | 8–36 |
| *Providencia stuartii* | 2 | 20 | 2–39 |
| *Klebsiella oxytoca* (2) | 5 | 13 | 2–41 |
| *Enterobacter cloacae* | 4 | 11 | 1–27 |
| *Acinetobacter calcoaceticus* | 3 | 8 | 2–14 |
| *Neisseria gonorrhoeae* | 2 | 7 | 1–12 |
| *Proteus mirabilis* | 1 | 4 | — |
| *Salmonella heidelberg* | 2 | 2 | 2 |
| TOTAL | 106 | 280 | 1–10030 |

[a]No. = number of experiments.
[b]Number appearing in parenthesis represents the number of isolates tested.

TABLE 7

BACTERICIDAL ACTIVITY AGAINST
GRAM POSITIVE ORGANISMS IN WHOLE BLOOD
Saponin/0.6% SPS Tube vs. Untreated

| Organism | No.[a] | Increased Recovery (#-fold improvement) | |
|---|---|---|---|
| | | Avg. | Range |
| *Staphylococcus epidermidis* | 2 | 15 | 10–21 |
| *Streptococcus faecalis* | 1 | 6 | — |
| *Streptococcus agalactiae* | 3 | 4 | 4–5 |
| *Streptococcus pneumoniae* (6)[b] | 24 | 2 | 0.3–9 |
| *Staphylococcus aureus* (2) | 8 | 2 | 1–2 |
| TOTAL | 38 | 6 | 0.3–21 |

[a]No. = number of experiments.
[b]Number appearing in parenthesis represents the number of isolates tested.

I claim:

1. In a method for testing a sample containing at least one blood component for the presence of microorganisms, wherein (a) said sample is mixed with sodium polyanethol sulfonate in a sufficient quantity to block humoral components present in said sample from exerting a tidal effect on microorganisms which may be present in said sample, to form a sodium polyanethol sulfonate-treated mixture; (b) an aliquot of said sodium polyanethol sulfonate-treated mixture is distributed onto a culture plate containing a nutritional agar media to form an inoculated culture plate in an aliquot to media ratio to provide sufficient dilution of said sodium polyanethol sulfonate-treated mixture to allow said microorganisms to replicate; (c) said inoculated culture plate is incubated for a sufficient period of time to allow colony forming units of said microorganisms present in said sample to form; and (d) said colony forming units are counted to quantitate said microorganisms, the improvement comprising adding a sufficient concentration of sodium polyanethol sulfonate at the time of forming said sodium polyanethol sulfonate-treated mixture such that sodium polyanethol sulfonate is maintained at a concentration from about 0.1% to about 1.0% up to the time of counting said colony forming units to quantitate said microorganisms.

2. The method of claim 1, further comprising mixing with said sample a sufficient quantity of a nontoxic blood lysing agent to lyse all cellular blood components present in said sample to form a lysed sample prior to plating onto said media.

3. The method of claim 2, wherein said nontoxic blood lysing agent comprises purified saponin.

4. The method of claim 3, wherein said purified saponin concentration is from about 0.1 mg/ml to about 20 mg/ml.

5. In a method for testing a sample containing at least one blood component for the presence of microorganisms, wherein (a) said sample is distributed onto a culture plate containing nutritional agar media to form an inoculated culture plate; (b) said inoculated culture plate is incubated for a sufficient period of time to allow colony forming units of said microorganisms present in said sample to form; and (c) said colony forming units are counted to quantitate said microorganisms, the improvement comprising adding sodium polyanethol sulfonate to said nutritional agar media such that the concentration of sodium polyanethol sulfonate is maintained at a concentration from about 0.005% to about 1.0% from the time of distributing said sample onto said culture plate to the time of counting said colony forming units to quantitate said microorganisms.

6. The method of claim 5, wherein said media further comprises a nontoxic blood lysing agent.

7. The method of claim 6, wherein said nontoxic blood lysing agent comprises purified saponin.

8. The method of claim 7, wherein said purified saponin concentration in said media is from about 0.1 mg/ml to about 20 mg/ml.

9. In a method for testing a sample containing at least one blood component for the presence of microorganisms, wherein (a) said sample is mixed with a sufficient quantity of a nontoxic blood lysing agent to lyse all cellular blood components present in said sample to form a lysed sample; (b) said lysed sample is mixed with sodium polyanethol sulfonate in a sufficient quantity to block humoral components present in said sample from exerting a cidal effect on microorganisms which may be present in said sample, to form a sodium polyanethol sulfonate-treated mixture; (c) an aliquot of said sodium polyanethol sulfonate-treated mixture is distributed onto a culture plate containing nutritional agar media to form an inoculated culture plate; (d) said inoculated culture plate is incubated for a sufficient period of time to allow colony forming units of said microorganisms present in said sample to form; and (e) said colony forming units are counted to quantitate said microorganisms, the improvement comprising adding sodium polyanethol sulfonate to said nutritional agar media such that the concentration of sodium polyanethol sulfonate is maintained at a concentration from about 0.005% to about 1.0% from the time of distributing said sample onto said culture plate to the time of counting said colony forming units to quantitate said microorganisms.

10. The method of claim 9, wherein said media further comprises a nontoxic blood lysing agent.

11. The method of claim 9, wherein said nontoxic blood lysing agent comprises purified saponin.

12. The method of claim 10, wherein said nontoxic blood lysing agent comprises purified saponin.

13. The method of claim 11, wherein said purified saponin concentration in said lysed blood sample is from about 0.1 mg/ml to about 20 mg/ml.

14. The method of claim 12, wherein said purified saponin concentration in said lysed blood sample and in said media in combination is from about 0.1 mg/ml to about 20 mg/ml.

15. In a method for testing a sample containing at least one blood component for the presence of microorganisms, wherein (a) said sample is mixed with sodium polyanethol sulfonate in a sufficient quantity to block humoral components present in said sample from exerting a cidal effect on said microorganisms which may be present in said sample, to form a sodium polyanethol sulfonate-treated mixture; (b) an aliquot of said sodium polyanethol sulfonate-treated mixture is distributed onto a culture plate containing a nutritional agar media to form an inoculated culture plate; (c) said inoculated culture plate is incubated for a sufficient period of time to allow colony forming units of said microorganisms present in said sample to form; and (d) said colony forming units are counted to quantitate said microorganisms, the improvement comprising adding sodium polyanethol sulfonate to said nutritional agar media such that the concentration of sodium polyanethol sulfonate is maintained at a concentration from about 0.1% to about 1.0% from the time of distributing said sample onto said culture plate to the time of counting said colony forming units to quantitate said microorganisms.

16. The method of claim 15, wherein said media further comprises a nontoxic blood lysing agent.

17. The method of claim 16, wherein said nontoxic blood lysing agent comprises purified saponin.

18. The method of claim 17, wherein said purified saponin concentration in said lysed blood sample and in said media in combination is from about 0.1 mg/ml to about 20 mg/ml.

19. In a method for determining the shelf-life of a stored blood product for transfusion purposes, wherein said blood product is tested for the presence of microorganisms and said blood product is discarded if any evidence of said microorganisms is indicated, the improvement comprising conducting a screening to quantitate microorganisms using a method in which sodium polyanethol sulfonate is maintained at a concentration from about 0.005% to about 1.0% from the time of sampling and continuing throughout a culturing process on nutritional agar media until any colony forming units are counted, to obtain a quantitative count of colony forming units, discarding said blood products only if said count exceeds 100 colony forming units per ml, utilizing or retaining said blood product for transfusion purposes if said count is less than 10 colony forming units per ml, and retaining said blood product for a retest if said count is between 10–100 colony forming units per ml, said retest utilizing same procedure as said screening, said retest conducted 24–48 hours after said count from said screening is obtained.

20. The method of claim 19, wherein said screening of said blood product is initiated after about 24 hours incubation at room temperature.

21. The method of claim 19, wherein said screening of said blood product is initiated after about 48 hours incubation at room temperature.

22. The method of claim 19 wherein said screening of said blood product is initiated after about ten days incubation at 4° C.

23. In a method for improving the recovery of microorganisms from broth-based blood culture techniques, wherein a sample containing blood cellular components is obtained and an aliquot thereof is distributed into a nutritional broth, said broth comprising sodium polyanethol sulfonate in an effective amount to block humoral factors which are cidal to said microorganisms which may be present in said sample, to form a broth blood culture, the improvement comprising the addition of a nontoxic blood lysing agent at a concentration such that the effective concentration of said sodium polyanethol sulfonate in combination with said nontoxic blood lysing agent is less than the effective concentration of said sodium polyanethol sulfonate alone.

24. The method of claim 23, wherein said nontoxic blood lysing agent comprises purified saponin.

25. The method of claim 24, wherein said purified saponin concentration is from about 0.1 mg/ml to about 20 mg/ml.

26. In a method for testing a sample containing at least one blood component for the presence of microorganisms, wherein said sample is mixed with sodium polyanethol sulfonate, said sodium polyanethol sulfonate being maintained in a sufficient quantity to block humoral components present in said sample from exerting a tidal effect on microorganisms which may be present in said sample, the improvement comprising said sodium polyanethol sulfonate is maintained at a concentration from about 0.005% to about 1% throughout said culturing method.

27. The culturing method of claim 26, wherein said sodium polyanethol sulfonate is maintained at a concentration from about 0.1% to about 1% throughout said culturing method.

* * * * *